United States Patent [19]

Willoughby, Jr. et al.

[11] Patent Number: 5,192,551
[45] Date of Patent: Mar. 9, 1993

[54] NEUTRAL GLYCOLIPID AS AN ADSORBENT FOR ENTERIC VIRAL PATHOGENS

[75] Inventors: Rodney E. Willoughby, Jr.; Robert H. Yolken, both of Baltimore, Md.

[73] Assignee: Johns Hopkins University, Baltimore, Md.

[21] Appl. No.: 346,450

[22] Filed: May 2, 1989

[51] Int. Cl.$^5$ .................. A61K 9/16; A61K 31/74
[52] U.S. Cl. ...................... 424/489; 424/78.08; 424/493; 514/23
[58] Field of Search .............. 424/450, 489, 78, 493, 424/78.08; 514/23; 436/511

[56] References Cited

U.S. PATENT DOCUMENTS

| 4,161,516 | 7/1979 | Bell | 424/489 |
| 4,315,001 | 2/1982 | Blough | 514/23 |
| 4,762,822 | 8/1988 | Ettinger | 514/25 |
| 4,786,592 | 10/1988 | Deal | 436/511 |
| 4,859,769 | 8/1989 | Karlsson | 536/1.1 |
| 4,906,562 | 3/1990 | Hellstrom | 436/514 |

FOREIGN PATENT DOCUMENTS 8603971 7/1986 World Int. Prop. O. .

OTHER PUBLICATIONS

Taki, et al., *J. Biochem*, 91:1813-1816 (1982), entitled: "Simple Purification Method for Anti-Glycolipid Antibody Using Polystyrene Latex Beads Coated with Gangliotetraosylceramide".
Holmgren, et al., *Eur. J. Biochem.*, 106:371-379 (1980), entitled: "Polystyrene-Adsorbed gangliosides for Investigation of the Structure of the Tetanus-Toxin Receptor".
Willoughby et al., *Pediactric Research*, vol. 25, No. 4, Part 2, (1989) Entitled: "Rotaviruses and Other Enteric Viruses Specifically Bind to Asialo GMA (GA$_1$)".
Tiemeyer et al., "Ganglioside-Specific Binding Protein on Rat Brain Membranes," J. Biol. Chem. (1989), 264:1671-1681.
Krivan et al., "Many Pulmonary Pathogenic Bacteria Bind Specifically to the Carbohydrate Sequence GalNAcb1-4Gal Found in Some Glycolipids," Proc. Natl. Acad. Sci. USA (1988), 85:6157-6161.
Willoughby et al., "SA11 Rotavirus is Specifically Inhibited by an Acetylated Sialic Acid," abstract from Society for Pediatric Research meetings, Apr., 1988, in Washington, D.C.
Yolken et al., "Sialic Acid Glycoproteins Inhibit in Vitro and In Vivo Replication of Rotaviruses," J. Clin. Invest. (1987), 79:148-154.
Flores et al, "The Role of Rotaviruses in Pediatric Diarrhea," Pediatric Infectious Disease (1986), 5:S53-S62.
Hill et al., "Use of Oral Gentamicin, Metronidazole, and Cholestyramine in the Treatment of Severe Persistent Diarrhea in Infants," Pediarics (1986), 77:477-481.
Moss et al., "Functional Incorporation of Ganglioside into Intact Cells: Induction of choleragen Responsiveness," Proc. Natl. Acad. Sci. USA (1976) 73:1034-1037.
Fields, "Molecular Basis of Reovirus Virulence," Archives of Virology (1982) 71:95-107.
Magnani et al., "Detection of Glycolipid Ligands by Direct binding of Carbohydrate-Binding Proteins to Thin-Layer Chromatograms," Methods in Enzymology (1982), 83:235-241.
Dahms et al., "Ganglioside Composition is Regulated During Differentiation in the Neuroblastoma×Glioma Hybrid Cell Line HG108-15," J. Neuroscience (1983), 3:806-817.
Umesaki, "Immunohistochemical and Biochemical Demonstration of the Change in Glycolipid Composition of the Intestinal Epithelial Cell Surface in Mice in Relation to Epithelial Cell Differentiation and Bacterial Association," J. Biochem. Cytochem. (1981), 32:299-304.
Bishop et al., "Virus Particles in Epithelial Cells of Duodenal Mucosa From with Acute Non-Bacterial Gastroenteritis," Lancet (1973), pp. 1281-1283.

Primary Examiner—Thurman K. Page
Assistant Examiner—G. S. Kishore
Attorney, Agent, or Firm—Banner, Birch, McKie and Beckett

[57] ABSTRACT

The binding of neutral glycolipid GA1 (asialo-GM1) to a broad spectrum of enteric viruses is taught. The glycolipid can be used to pass through the gastrointestinal tract of adults and children to adsorb viral particles and remove them from the body. The glycolipid may be used alone or bound to a non-absorbable resin or matrix.

8 Claims, 3 Drawing Sheets

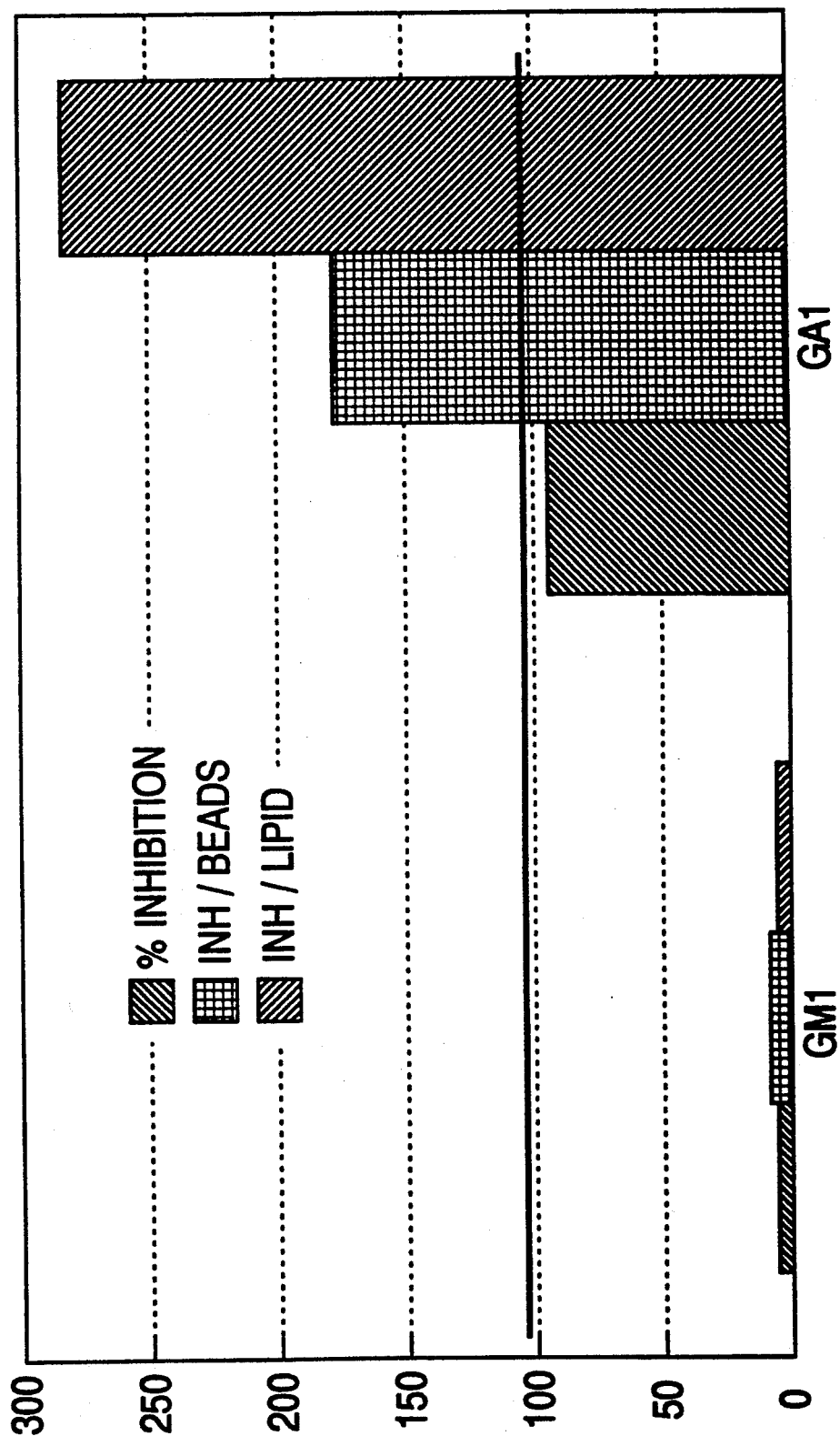

NEUTRAL GLYCOLIPID AS AN ADSORBENT FOR ENTERIC VIRAL PATHOGENS

The U.S. States Government has a paid-up license in this invention and the right in limited circumstances to require the patent owner to license others on reasonable terms as provided for by the terms of grant number 5-K12DK01298-05 awarded by the National Institutes of Health.

BACKGROUND OF THE INVENTION

Since its discovery 15 years ago, rotavirus has been recognized as the single most common etiologic agent of gastroenteritis in infants requiring hospitalization, in developed and developing countries alike. Rotaviruses are RNA virus of the family Reoviridae. While rotaviruses are known to replicate in a number of tissue culture cell lines and in the intestinal epithelial cells of a wide range of animal species, little is known about the nature of the interactions of rotaviruses with cells that support rotaviral replication. Sialic acid-containing glycoproteins have been identified which bind directly to rotaviruses. Yolken, et al., Jour. of Clin. Invest., Vol. 79, pp. 148–154, 1987.

Despite the important advances of biomedical research in the last decades that have led to the development of sophisticated therapeutic techniques, diarrheal diseases continue to be a major cause of mortality among infants and young children in the developing world. Thus there is a need in the art for methods and products for treating enteric viral diseases leading to diarrhea in children.

SUMMARY OF THE INVENTION

It is an object of the invention to provide a method of treating a human or other mammal to prevent or diminish viral infections.

It is another object of the invention to provide a composition for preventing enteric viral infections in infants.

It is yet another object of the invention to provide a composition for treating children and adults infected with enteric viruses.

It is still another object of the invention to provide a composition for preventing and treating enteric viral infections. These and other objects of the invention are provided by one or more of the embodiments described below.

In one embodiment of the present invention a method is provided of treating a human or other mammal to prevent or diminish enteric viral infections, comprising: orally administering an effective amount of gangliotetraosylceramide to a human or other mammal to bind enteric viruses.

In another embodiment of the invention a composition is provided comprising an infant nutrient formula and an effective amount of gangliotetraosylceramide for binding to enteric viruses.

In still another embodiment of the invention a composition is provided comprising: a rehydration formula and an effective amount of gangliotetraosylceramide for binding to enteric viruses.

In yet another embodiment of the present invention a composition is provided, comprising: gangliotetraosylceramide bound to a non-absorbable support.

The present invention provides the art with a prophylactic and therapeutic means for readily treating diarrheal diseases which are a major cause of mortality among infants and young children in the developing world. The treatment and prophylactic means are simple to administer and so do not require intervention by medical personnel or use of high technology facilities.

BRIEF DESCRIPTION OF THE DRAWINGS

FIGS. 1a and b show the binding of radiolabeled SA11 rotavirus to chromatographically separated neutral glycolipids. FIGS. 1a and b show the chromatographic separation of neutral glycolipids stained by char.

FIGS. 2a and b show the thin layer chromatogram; area A represents nonpolar lipids (cholesterol and triglycerides, etc.) and area B represents neutral glycolipid GA1. Panel B shows an autoradiogram of the polyacrylamide gel with viral proteins identified.

FIG. 3 shows the neutralizing effect of GA1-coated beads on the infectivity of SA11 rotavirus for cell cultures. The neutralizing effect of GM1-coated beads is also shown.

DETAILED DESCRIPTION

Figure 1B:
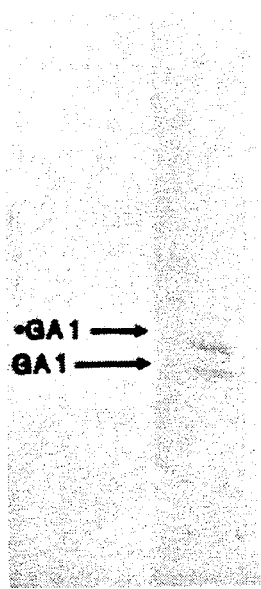
FIGS. 1a and b show the effect of galactose oxidase treatment of neutral glycolipid on the binding of viruses to GA1.

It is a discovery of the present inventors that a broad range of enteric viruses which are pathogenic to humans and other mammals are bound by a single glycolipid molecule, namely gangliotetraosylceramide (GA1). This is surprising in view of the fact that these viruses are known to bind to different cellular receptors. This is also surprising because gangliotetraosylceramide is a neutral glycolipid, whereas some Reoviridae have already been shown to bind to acidic glycoproteins. The glycolipid of the present invention, also known as asialo-GM1 as well as GA1, can be used to treat humans both preventively, i.e., as a prophylactic, as well as therapeutically, i.e., after infection to diminish the severity of infection. While human enteric viruses have been found to bind to GA1, other viruses may also employ GA1 as a common binding mechanism to cells. For example, animal viruses may bind to GA1, as there is evidence that GA1 exists in mouse enterocytes. In addition, other viruses of humans may bind to GA1, for example, respiratory viruses, such as adenovirus, influenza, parainfluenza, and respiratory syncytial virus.

According to the method of the present invention the gangliotetraosylceramide is orally administered. The GA1 glycolipid may be obtained commercially, for example from the Sigma Chemical Co., St. Louis, Mo. GA1 can also be prepared by acid hydrolysis of GM1 glycolipid as described in Dahms, et al., J. Neuroscience, vol. 3, pp. 806–817, 1983. As this neutral glycolipid is acid-stable, it does not need to be protected to survive in the gastrointestinal tract. However, it may be desirable to bind the neutral glycolipid to a non-absorbable support. The selection of a support is within the skill of the art and such supports include beads, resins, natural or synthetic polymers. One particularly preferred non-absorbable support is cholestyramine, which has previously been shown to be effective as an antidiarrheal agent for bacterial pathogens. The neutral glycolipid may be bound to the non-absorbable support via a simple absorption or via a covalent linkage. Methods for performing both such types of binding are well known in the art. (See, e.g., Tiemeyer, et al., J. Biol. Chem., vol. 264, pp. 1671-1681, 1989, and Taki, et al., J. Biochem. vol. 91, pp. 1813-1816, 1982.) If absorption is to be used as the means of attachment, a hydrophobic bead is preferred.

Other means of administering the neutral glycolipid of the present invention involve forming small lipid particles comprising the gangliotetraosylceramide. Such lipid particles may be, for example, vesicles, micelles, or liposomes. In addition, the gangliotetraosylceramide may be administered in the form of a capsule or tablet. Suitable formulations can be prepared according to methods well known in the art. See, e.g., Remington's Pharmaceutical Sciences, Mack Publishing Co., Easton, Pa., latest edition. Although applicants do not wish to be bound by any particular theory, it is thought that bound or particulate forms of the neutral glycolipid may be desirable in order to keep a high local density of the glycolipid.

As a treatment for diarrhea, the neutral glycolipid of the present invention has benefits over traditional antibiotic therapy. Antibiotics have the undesirable characteristic of being effective against normal gastrointestinal bacterial colonizers. Thus antibiotic therapy often leads to infection by secondary infectious agents because the antibiotic has eliminated the normal competitors for the particular ecological niche.

Rehydration formulae are often administered to replenish electrolytes which are lost due to severe diarrhea. In some cases they are administered intravenously, and in other cases oral administration is successful. In one embodiment of the present invention it is contemplated that at effective amount of the gangliotetraosylceramide will be admixed with a rehydration formula for administration to a patient suffering from diarrhea. Sufficient gangliotetraosylceramide should be administered to bind to a substantial portion of the enteric viruses causing the infection so that the infection is diminished. Rehydration formulae are well known in the art and are commercially available.

In another embodiment of the present invention it is contemplated that the gangliotetraosylceramide of the present invention will be administered in an infant nutrient formula. Once again, an effective amount of the gangliotetraosylceramide must be used to bind to enteric viruses in the gastrointestinal tract. Infant nutrient formulae are well known in the art and are commercially available. The infant nutrient formula containing the neutral glycolipid of the present invention may be given to children routinely in areas where diarrhea is endemic. Alternatively, when a viral diarrhea outbreak is occurring, for example in a hospital, infants can be given the nutrient formula of the present invention in order to prevent spread of the infection to uninfected infants as well as to treat infected infants.

An effective amount of gangliotetraosylceramide according to the present invention is one that is effective to bind to the targeted viruses. Generally, for oral administration, this will be between about 10 uM and about 1 mM. Preferably, between about 12 ug and 1.2 mg will be administered to a child and between about 200 ug and 10 mg will be administered to an adult.

In the case of treatment for respiratory viruses, a different mode of administration is used from that used for gastrointestinal tract infections. In order to reach the pharyngeal colonizers, the glycolipid of the present invention must be aerosolized. This can be accomplished by use of a nebulizer or a gargle. Such aerosolization techniques are well known in the art. Doses can be determined according to routine testing procedures which correlate amount administered with lowered titer of virus.

The following experimental data are presented to exemplify the invention. The invention is however not limited to these examples but is defined by the foregoing description and the claims which follow.

EXAMPLE 1

This example demonstrates that rotavirus SA11 binds with high specificity to glycolipid GA1.

Virus SA11 was grown in MA 104 cells, which are from a rhesus monkey kidney-derived cell line (available from MA Bioproducts, Walkersville, Md.) using previously described methods. (Hoshino, et al., Infect. Immun. 41:169-173, 1983.)

Various amounts of glycolipids were spotted on high performance thin layer chromatography plates (glass-backed silica gel plates, 0.2 mm thick, available from Merck, Darmstadt, Germany). The plates were developed in chloroform-methanol-0.25% KCl (60:35:8). After plasticizing with polyisobutyl-methacrylate and blocking with polyvinylpyrrolidone, (available from Sigma Chemical Co., St. Louis, Mo.,) as described in Magnani, et al., (Methods in Enzymology, vol. 83, pp. 235-240, 1982,) the glycolipids were probed with labeled virus SA11.

Two methods of labeling the virus were used, metabolic labeling with $^{35}S$-methionine and oxidative labeling with $^{125}I$-iodine. All viruses were purified on isopycnic cesium chloride gradients or on metrizamide gradients.

Rotavirus SA11 bound to: GA1 at concentrations as low as 30 pmol; to neolactotetraosylcermide (nLc$_4$) at concentrations of 500 pmol and above; and to other glycolipids (Gb$_4$, G$_{A2}$, Lac, G$_{D1a}$, G$_{M1}$, G$_{M3}$) only at concentrations greater than 1000 pmol.[1] GA1 and nLc$_4$ differ only in the substitution of an N-acetyl-glucosamine moiety for an N-acetyl-galactosamine moiety.

Lac=Gal(beta)1 - 4 Glc (beta)1 - 1Cer; G$_{D1a}$=NeuAc(alpha)2 -3 Gal(beta)1 - 3 Gal - NAc(beta)1 - 4(NeuAc (alpha)2-3) Gal(beta)1 - 4Glc(beta)1 - 1Cer; GM1=gal(beta)1 - 3 Gal NAc(beta)1 - 4 (NeuAc-(alpha)2-3) Gal(beta)1 - 4 Glc(beta)1- 1Cer; G$_{M3}$=NeuAc(alpha)2 - 3 Gal(beta)1 - 4 Glc(beta)1 - 1 Cer; G$_{A2}$=Gal NAc(beta)1 - 4 Gal(beta)1 - 4 Glc(beta)1 - 1 Cer; G$_{A2}$=GalNAc(beta1 - 4 Gal(beta)1 - 4 Glc(beta)1 - 1 Cer; GA1=Gal(beta)1 - 3 Gal Nac(beta)1 - 4 Gal(beta)1 - 4 Glc(beta)1 - 1Cer; Gb$_4$=GalNAc(beta)1 - 4 gal(beta)1 - 4 Gal(beta)1 - 4 Glc(beta)1 - 1 Cer; nLc$_4$=4 Gal(beta)1 - 4 GlcNAc(beta)1 - 4 Gal(beta)1 - 4 Glc(beta)1 - 1 Cer.

EXAMPLE 2

This example demonstrates that the binding of SA11 rotavirus is exquisitely specific for the GA1 molecule. Enzymatic oxidation of the terminal galactose abolishes virus binding.

GA1 glycolipid was treated with the enzyme galactose oxidase (1 unit) as well as 4 units of horseradish peroxidase and 20 units of catalase in 50% tetrahydrafuran overnight at room temperature, and the products were chromatographically separated as described in Example 1. The chromatogram was visualized using char (10% H$_2$SO$_4$ and 50% EtOH in water and baked at 120° C. for 10-15 min.

Figure 1A:

As shown in FIG. 1b, most of the GA1 was converted to the oxidized (aldehyde) form which is faster migrating than genuine GA1. When the chromatogram was probed with radiolabeled SA1 rotavirus, only genuine GA1 bound virus; the oxidized form bound no detectable SA11 virus. (See FIG. 1(a). *GA1 indicates the migration position of the oxidized form of GA1.

This experiment shows the specificity of binding of the SA11 virus to the GA1 glycolipid. Chemical oxidative treatment of GA1 with periodate also abolishes SA11 virus binding.

EXAMPLE 3

This example demonstrates that the SA11 virus binding to GA1 is mediated through an interaction with viral protein VP7.

Figure 2A:
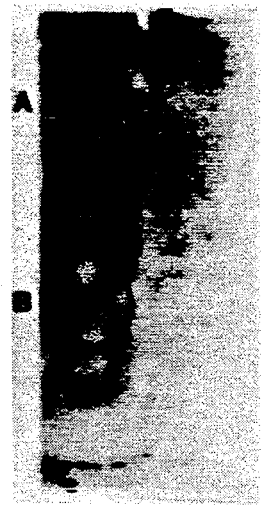
FIGS. 2a and b show a polyacrylamide gel of electrophoretically separated virus proteins which had previously bound to chromatograms containing various glycolipids.
Figure 2B:
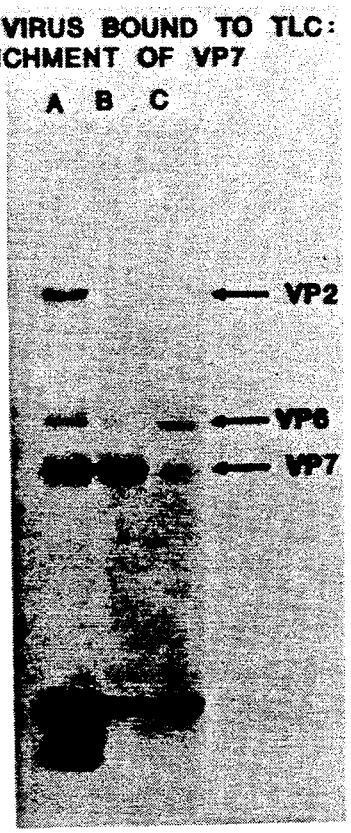

Glycolipids were separated on a chromatogram, as described in Example 1, and probed with radiolabeled SA11 virus. Two regions of binding were scraped from the plate, one corresponding to the migration of GA1 and the other corresponding to large amounts of nonpolar lipids. These two regions are labeled B and A, respectively, in FIG. 2(a). The proteins in the scrapings were solubilized in Laemmli sample buffer and run on 10% polyacrylamide gels. (See FIG. 2(b)). Lane (a) which contains protein scraped from region A shows that many different viral proteins bound to the glycolipid spot containing nonpolar lipids, whereas the GA1 glycolipid bound predominantly protein VP7 (Lane (b)). Lane (c) shows the migration of labeled viral proteins which had not been pre-bound to the chromatogram.

Binding of SA11 rotavirus to GA1 can be blocked by neutralizing antibodies (directed against VP7). However, antibodies raised against VP7 of other serotypes do not block SA11 binding to GA1.

EXAMPLE 4

This example demonstrates that all non-enveloped enteric viruses tested exhibit binding to GA1 glycolipid.

Rotaviruses (Wa, DS-1, SA11, MMU 18006, NCDV), Reoviruses (1 and 3), Poliovirus 1, and Coxsackievirus 3 were propagated in Ma104 cells. Coxsackievirus A4 was propagated in RD cells (a rhabdosarcoma cell line). The viruses were either metabolically labeled with $^{35}$S-methionine and purified or purified and then labeled with $^{125}$I-iodine. Purification of viruses was by isopycnic cesium chloride gradients or by metrizamide gradients.

The ability to bind to GA1 was assessed by binding the radiolabeled viruses to glycolipids resolved on thin layer chromatography plates by the method of Magnani, supra. All viruses tested bound to GA1. Bovine serum albumin, labeled with $^{125}$I did not bind to GA1. Poliovirus 1 bound to GA1 when it was labeled with $^{35}$S-methionine, but not when labeled with $^{125}$I. This is consistent with references in the literature reporting that the harsh conditions employed to radioiodinate proteins destroy poliovirus infectivity.

EXAMPLE 5

This example demonstrates that GA1 bound to polystyrene beads is able to reduce-viral infectivity.

GA1 (asialo GM1) and GM1 were bound to polystyrene beads by the method of Taki, et al. (J. Biochem., vol. 91, pp. 1813-1816, 1982). Briefly, the glycolipids are dispersed in water and the dispersion is heated to 80° C. just long enough so that the lipids go into solution. The polystyrene beads are then mixed into the solution and the glycolipids adsorb onto the beads.

The glycolipid-coated beads were then mixed with crude SA11 viral lysates and incubated at 37° C. for 60 min. The beads were removed by centrifugation and the supernatant was used to infect Ma104 cells.

The difference in numbers of plaques formed in the control infections (virus alone) and in the infections with GM1-bead treated and GA1-bead treated lysates are shown in FIG. 3. On a per lipid basis, GA1 inhibited viral infections 50-fold greater than GM1. GA1 inhibition of viral infections was essentially complete.

When a different method (Roseman, et al., unpublished, adapted from Schnaar) was used to bind glycolipids to the polystyrene beads the absolute magnitude of the inhibition was greatly reduced. This method involves the dissolving of GA1 in 50% ethanol followed by the evaporation of the aqueous component. Although the relative inhibition of GA1 was still much greater than GM1, globoside, GM3, and GD1a. Although the inventors do not wish to be bound by any particular theory, it is believed that the difference is due to the greater number of glycolipids which bind to the beads by the Taki method leading to a higher density of glycolipids per bead.

We claim:

1. A method of treating a human or other mammal to prevent or diminish enteric viral infections comprising orally administering gangliotetraosylceramide to said human or other mammal to bind to enteric viruses in an amount effective to prevent or diminish enteric viral infections.

2. The method of claim 1 wherein the amount of gangliotetraosylceramide is between about 12 micrograms and about 10 mg.

3. The method of claim 1 wherein the enteric viruses are non-enveloped.

4. The method of claim 3 wherein the enteric viruses are selected from the group consisting of rotaviruses, reoviruses, polioviruses, and coxsackie viruses.

5. The method of claim 1 wherein the gangliotetraosylceramide is bound to an enterically non-absorbable support.

6. The method of claim 5 wherein the non-absorbable support is a hydrophobic bead.

7. The method of claim 5 wherein the gangliotetraosylceramide is bound to the enterically non-absorbable support by adsorption.

8. The method of claim 5 wherein the gangliotetraosylceramide is bound by a covalent linkage.

* * * * *